United States Patent [19]
Rhodes

[11] Patent Number: 5,615,670
[45] Date of Patent: Apr. 1, 1997

[54] POWDER INHALER WITH CENTRIFUGAL FORCE USED TO METER POWDER

[75] Inventor: Ian Rhodes, Hertfordshire, England

[73] Assignee: Fisons plc, Ipswich, United Kingdom

[21] Appl. No.: 468,766

[22] Filed: Jun. 6, 1995

Related U.S. Application Data

[63] Continuation of Ser. No. 210,253, Mar. 18, 1994, abandoned, which is a continuation of Ser. No. 934,445, Sep. 4, 1992, abandoned.

[30] Foreign Application Priority Data

Mar. 7, 1990 [GB] United Kingdom ............... 90/05110

[51] Int. Cl.$^6$ .................. A61M 15/00; A61M 16/00; B05D 7/14; B65D 83/06
[52] U.S. Cl. ................ 128/203.15; 128/203.23
[58] Field of Search .............. 128/203.15, 203.21, 128/203.23, 203.12, 203.14; 222/162, 169, 507, 337; 604/56

[56] References Cited

U.S. PATENT DOCUMENTS 4,116,195 9/1978 James ................ 128/203.21
4,805,811 2/1989 Wetterlin ................ 222/337
5,048,514 9/1991 Ramella ................ 128/203.15

FOREIGN PATENT DOCUMENTS 0166294 1/1986 European Pat. Off. .
2041763 9/1980 United Kingdom .

Primary Examiner—Kimberly L. Asher
Attorney, Agent, or Firm—Marshall, O'Toole, Gerstein, Murray & Borun

[57] ABSTRACT

A device for the administration by inhalation of a medicament in dry powder form comprises a medicament reservoir (9) and a medicament metering system (10) including a metering chamber (23) communicable with the reservoir (9), characterized in that the reservoir (9) is mounted in a housing (1) for rotation about an axis and the metering chamber (23) is located radially of the axis, the arrangement being such that the metering chamber (23) is charged with medicament during a charging rotation of the reservoir (9) about the axis.

8 Claims, 5 Drawing Sheets

POWDER INHALER WITH CENTRIFUGAL FORCE USED TO METER POWDER

CROSS-REFERENCE TO RELATED APPLICATIONS

This application is a continuation of U.S. application Ser. No. 08/210,253, filed on Mar. 18, 1994, now abandoned, which was a continuation of U.S. application Ser. No. 07/934,445, filed Sep. 4, 1992, now abandoned.

BACKGROUND OF THE INVENTION

1. Field of the Invention

This invention relates to a device for the administration by inhalation of a medicament in dry powder form, which comprises a medicament reservoir and medicament metering means including a metering chamber communicable with the reservoir.

2. Description of the Prior Art

Devices for the administration by inhalation of medicaments in dry powder form are well known. European Patent Application No 166294 discloses such a device comprising a medicament reservoir and a metering chamber with a volume chosen such that, when filled, the chamber contains the desired weight of medicament for a dose. Filling of the metering chamber is accomplished under the influence of gravity, the chamber being located at the bottom of the reservoir. This passive method of charging the metering chamber suffers from the disadvantage that variations in the density of the metered powder can easily occur resulting in inaccurate or inconsistent dosing. The packing density of the powder may also depend on the weight of powder remaining in the reservoir, leading to a gradual reduction in the dose delivered by the device. In addition, the dose metered is strongly dependent on the orientation of the device.

SUMMARY OF THE INVENTION

We have now found that these disadvantages can be overcome or substantially mitigated by a device which relies not on gravitational force to fill the metering chamber, but on a centrifugal force generated by rotation of the reservoir.

Thus, according to the invention there is provided a device for the administration by inhalation of a medicament in dry powder form, which comprises a medicament reservoir and medicament metering means including a metering chamber communicable with the reservoir, characterized in that the reservoir is mounted in a housing for rotation about an axis and the metering chamber is located radially of the axis, the arrangement being such that the metering chamber is charged with medicament during a charging rotation of the reservoir about the axis.

The device according to the invention is advantageous over other, known devices in that it provides a more uniform and consistent dose of medicament, thus resulting in optimum therapeutic effect for the user. The device is also advantageous in that the quantity of medicament dispensed is largely independent of the orientation of the device when it is operated.

Preferably, the reservoir and the metering chamber are relatively displaceable such that in a metering position the metering chamber communicates with the reservoir, and in a dosing position the metering chamber communicates with a mouthpiece. Such an arrangement may be achieved by various means. We prefer the reservoir to be displaceable along the axis of the device. It may then reciprocate with metering means which are not displaceable along the axis of the device.

It will be appreciated by those skilled in the art that the device of the present invention may be used for the administration of medicaments by inhalation to the nose, so that the term 'mouthpiece' should be interpreted to include structures suitable for insertion into the nose for inhalation of medicament from the device, as well as structures suitable for insertion into the mouth.

The metering chamber may take any convenient form, for example it may be a circumferential groove formed in the metering means, or it may be a perforated membrane of the type described in UK Patent No 2144997. It is however preferred that the metering chamber be a cavity formed in the metering means, for example a dish-shaped cavity.

There may be more than one metering chamber, and the use of more than one metering chamber is preferred since it may improve the uniformity of dose dispensed.

The metered dose of medicament may be inhaled directly from the metering chamber. Alternatively, the dose may be discharged into a suitable receptacle from which it may subsequently be inhaled. Means may be provided to aid dispersion of the powdered medicament; for example vanes, a grid or venturi may be provided to induce turbulence in the inhaled airflow.

We prefer the metering means to be mounted in the housing for concerted rotation with the reservoir. This is particularly advantageous when the metering chamber is a cavity and the reservoir communicates with the cavity through a small outlet, since the outlet and the cavity may then be disposed so that only axial displacement is needed to bring them into register. In a preferred embodiment, the metering means defines a swirl chamber communicating with the mouthpiece, which is adapted to receive an outlet end of the reservoir. The metering chamber may then be a cavity in the wall of the swirl chamber.

We have found that accurate metering is attained when the reservoir rotates at between 500 and 2000 rpm during the charging rotation, for example 1000 rpm. It will, however, be recognized that the optimum rotational speed will depend, inter alia, on the medicament, the radial distance of the metering chamber from the axis of rotation of the reservoir and the degree of rotation of the reservoir during the charging rotation. For example, satisfactory results may be obtained when the reservoir rotates through an angle of around 120° at 2000 rpm, or when it rotates through 1440° (4 revolutions) at 700 rpm, using pelletized sodium cromoglycate (prepared according to UK Patent No 1520247). Suitably, the radial distance of the metering chamber from the axis of rotation of the reservoir is in the range of 0.5 to 2 cm. Other medicaments which may be mentioned include nedocromil sodium and tipredane.

Rotation of the reservoir may be brought about manually, for example by the user spinning an accessible portion of the reservoir using the thumb of the hand holding the device. In order to improve the consistency of the dose dispensed, however, it is desirable to include a mechanism to ensure that the number of rotations and the rotational speed are repeatable. This may be achieved by using the force of relaxing biassing means to effect the charging rotation. Suitable biassing means include springs, more particularly torsion springs. The device may then be conveniently activated by rotation of the reservoir about the axis against the bias of the biassing means.

It is further envisaged that a small electric motor may be used to rotate the reservoir.

Desirably, relative displacement of the metering chamber and the reservoir from the dosing position to the metering position occurs during activation of the device. This has the advantage that fewer operations must be performed by a patient to administer a dose.

The reservoir is conveniently generally cylindrical. It is preferred that at least part of a main body of the interior of the reservoir be of relatively small radius so that the bulk of the medicament contained is subjected to only a low centrifugal force during the charging rotation. An outlet portion, conveniently located at a mouthpiece end of the reservoir and extending radially, communicating with both an outlet of the reservoir and the main body of the reservoir via a neck, may then be provided to enable the main body of the reservoir to communicate with the outlet.

We have found it particularly advantageous to provide an arrangement such that flow of powder from the main body of the reservoir into the outlet portion occurs freely but flow of powder in the reverse direction is inhibited or prevented. This effect may be achieved by making the neck venturi-shaped.

If the neck has steep sides on the side facing the main body of the reservoir, then powder will flow freely into the outlet portion when the device is upright: if the neck has less steep sides on the side facing the outlet portion, then medicament bridges the neck on that side and does not flow back into the main body of the reservoir, even when the device is inverted.

This is advantageous in that the outlet portion takes in medicament from the main body of the reservoir whenever the device is orientated so that the outlet portion lies below the main body of the reservoir, and once within the outlet portion, does not flow back into the main body of the reservoir. The outlet portion is thus always filled sufficiently to permit accurate dosing of medicament even when the device is operated with the outlet portion uppermost.

Typically, the neck will have sides at an angle of 30° or less to the vertical (when the device is upright) on the side of the main body of the reservoir, and sides at an angle of 45° or more to the vertical on the side of the outlet portion.

It is preferred that the reservoir is a discrete unit which may be readily replaced. This would enable spare reservoirs, both empty and containing refills of medicament, to be supplied separately, allowing the device to be at least partially reusable. According to another aspect of the invention, therefore, there is provided a reservoir for use in a device as defined above.

BRIEF DESCRIPTION OF THE DRAWINGS

A preferred embodiment of the device will now be described, by way of example, with reference to the accompanying drawings, in which.

DESCRIPTION OF THE PREFERRED EMBODIMENTS

Figure 1:
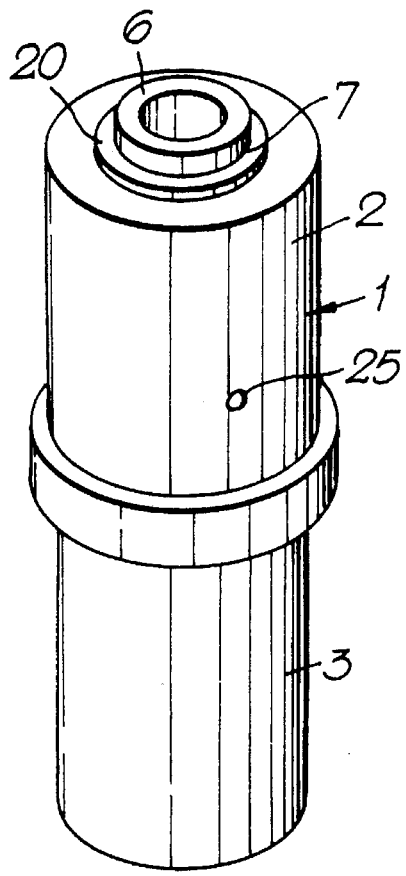
FIG. 1 is a perspective view of a device according to the invention.

Referring first to FIG. 1, a device for the administration by inhalation of a medicament in dry powder form comprises a cylindrical housing 1 having an upper housing portion 2 and a lower housing portion 3 which are relatively rotatable about the central axis of the device. A generally cylindrical mouthpiece 6 protrudes through an aperture 7 in the top surface of upper housing portion 2.

Figure 2:
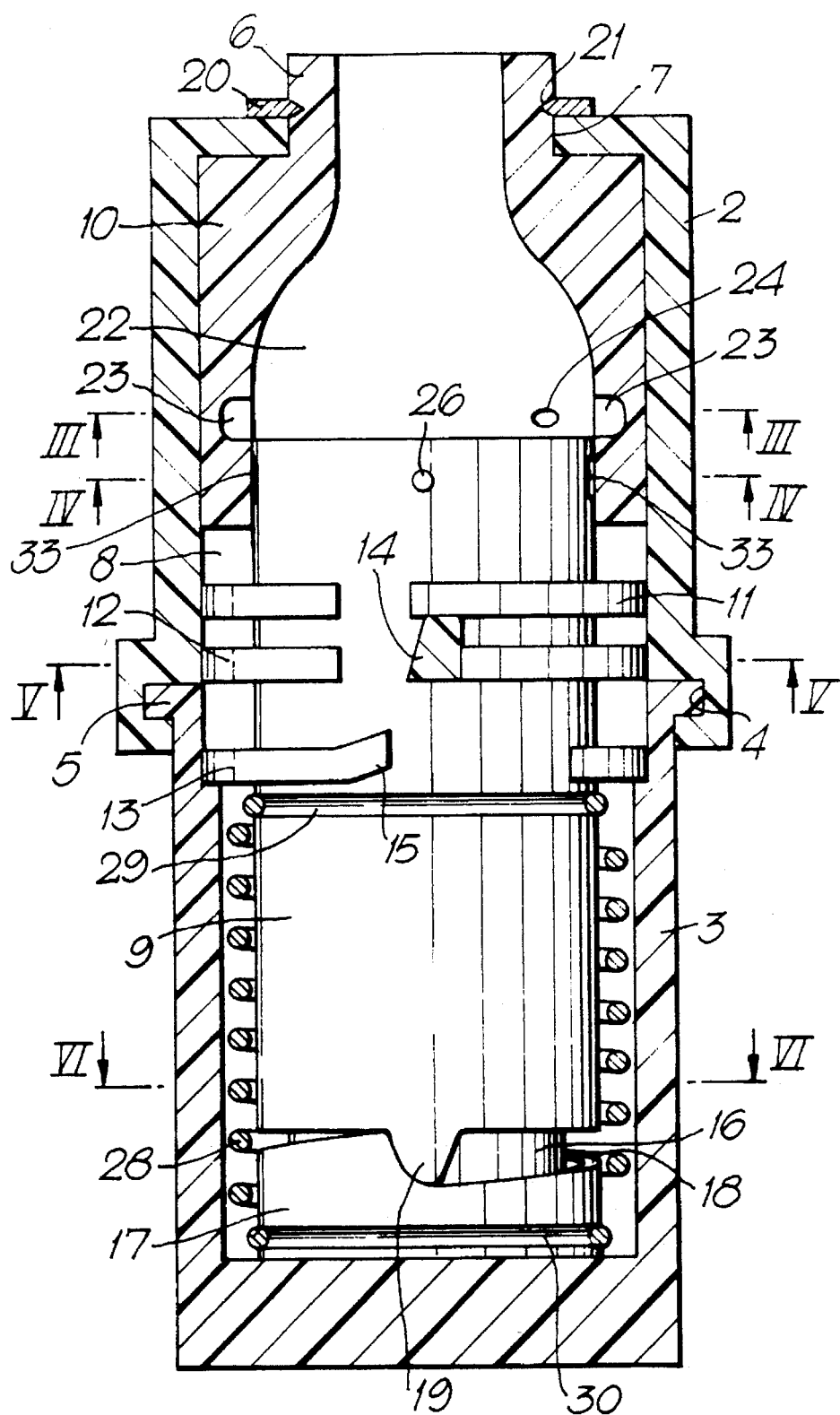
FIG. 2 is a side view of the device of FIG. 1 in a dosing position, partly cut away.

As can be seen from FIG. 2, upper housing portion 2 is provided with a circumferential groove 4 towards the base of its inner surface which retains an outwardly directed corresponding flange 5 formed at the top of lower housing portion 3. Flange 5 is free to slide within groove 4. The base of upper portion 2 is resiliently deformable to allow insertion of lip 5 into groove 4. In an alternative embodiment, the base of groove 4 is detachable to allow insertion of lip 5.

Housing 1 defines a cylindrical chamber 8 which houses a generally cylindrical reservoir 9 and a generally cylindrical metering member 10. Reservoir 9 and metering member 10 are rotatable about their central axes which are coaxial with the central axis of the device.

Reservoir 9 is provided with three interrupted circumferential ribs 11, 12, 13 which cooperate with a lug 14 provided on the inner surface of upper housing portion 2. The lower rib 13 has a ramp portion 15 at a trailing end which is directed towards the top of the device.

A reduced diameter portion of reservoir 9 forms an axle member 16 which is received in a bearing 17 in the form of a circular wall formed on the inner surface of the base of housing portion 3. The upper surface of bearing 17 defines a helical ramp 18 which bears upon a tongue 19 of reservoir 9.

Figure 3:
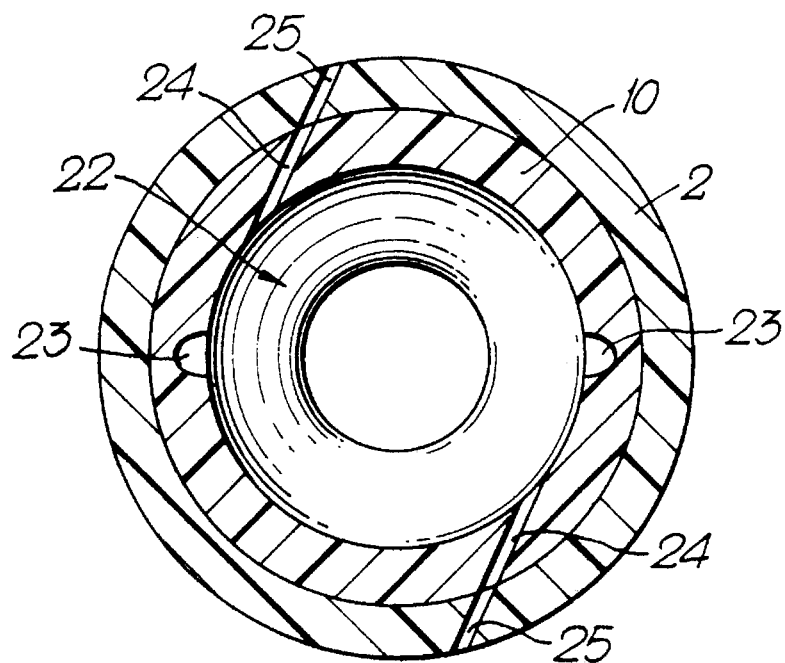
FIG. 3 is a lateral section along the line III—III of FIG. 2.
Figure 4:
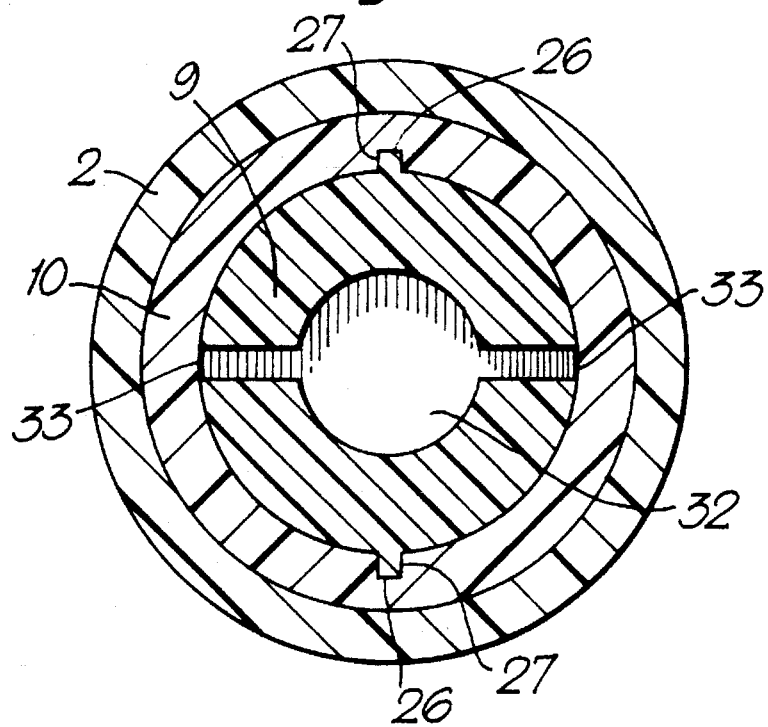
FIG. 4 is a lateral section along the line IV—IV of FIG. 2.
Figure 5:
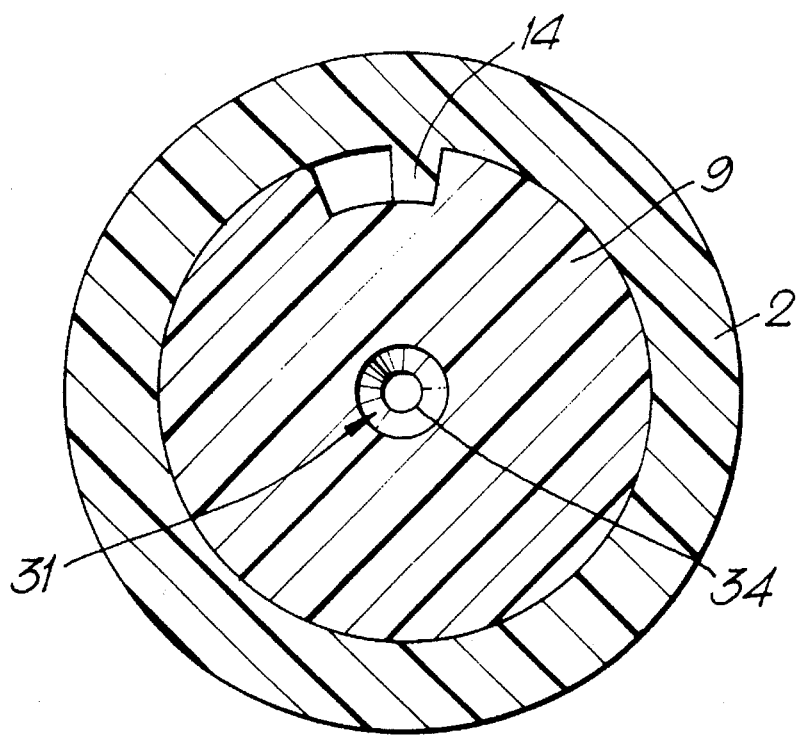
FIG. 5 is a lateral section along the line V—V of FIG. 2.
Figure 6:
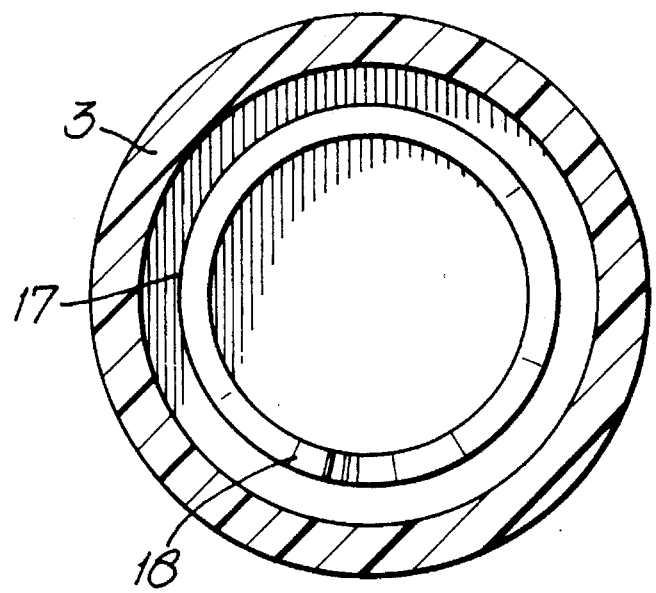
FIG. 6 is a lateral section (omitting a reservoir and a torsion spring) along the line VI—VI of FIG. 2.

Metering member 10 is retained in upper housing portion 2 by a ring 20 having an inwardly directed circumferential rib which is received in a circumferential groove 21 at the base of integral mouthpiece 6. Ring 20 may be resiliently deformable or formed in two parts to facilitate fitting onto mouthpiece 6. Metering member 10 defines a generally cylindrical swirl chamber 22 which tapers to an outlet in mouthpiece 6. Two metering cups 23 are provided on opposite sides of swirl chamber 22, into which tangential air inlets 24 through the wall of swirl chamber 22 are directed. In the dosing position, inlets 24 are aligned with inlets 25 (best seen in FIG. 3) through upper housing portion 2.

In an alternative embodiment, an air inlet is provided through upper housing portion 2 directly into chamber 8. A groove is provided on the outer surface of reservoir 9 which, in the dosing position, forms a conduit with the inner wall of swirl chamber 22 which conducts inhaled air from chamber 8 into metering chamber 23, thus emptying metering chamber 23.

Reservoir 9 is provided with two oppositely disposed pins 26 which extend radially from towards the top of its curved surface. These locate in longitudinal slots 27 formed in metering member 10, such that reservoir 9 and metering member 10 rotate together and reservoir 9 is upwardly displaceable from the dosing position along the central axis of the device.

A top end of a torsion spring 28 is anchored in a circumferential groove 29 in the middle of the curved surface of reservoir 9, and a bottom end is anchored in a circumferential groove 30 in the base of bearing 17. Spring 28 is under moderate tension in the dosing position (for example it may exert a force of 3 to 4N).

Figure 7:
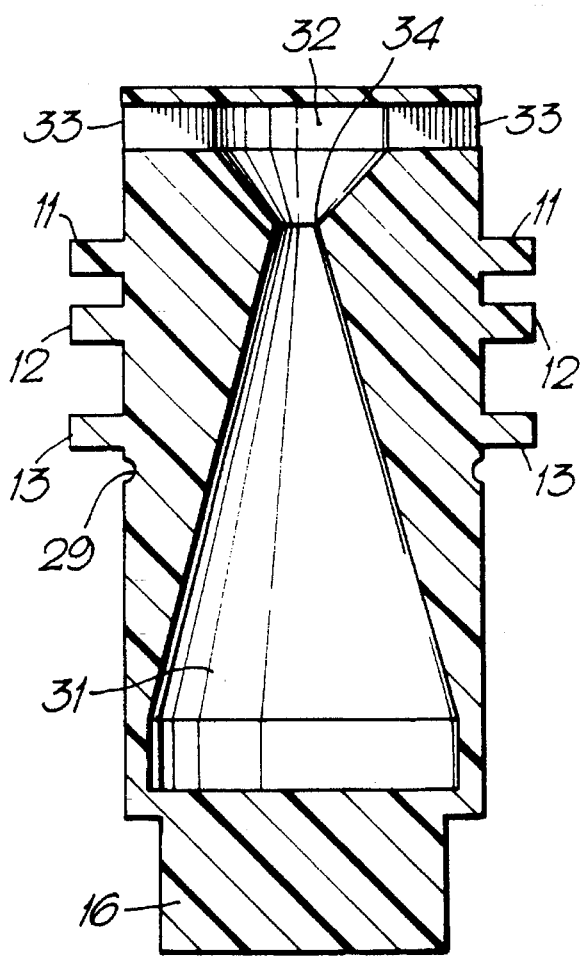
FIG. 7 is a longitudinal section of the reservoir in the plane of FIG. 2.

As is best shown in FIG. 7, reservoir 9 defines a generally frusto-conical main chamber 31 for inhalation of medicament in powdered form, and an outlet portion 32 which communicates with two outlets 33. Main chamber 31 and outlet portion 32 communicate via a venturi-shaped neck 34, the angle of the walls of outlet portion 32 to the central axis being greater than the angle of the walls of main chamber 31 to the central axis so that medicament moves easily from main body 31 into outlet portion 32, but is inhibited from returning.

Housing 1, reservoir 9 and metering member 10 are conveniently made of plastics material.

In the dosing position, lug 14 abuts a leading end of rib 12 and the lower surface of rib 11. Also, outlets 33 are sealed by the inner wall of swirl chamber 22. To activate the device, upper housing portion 2 is rotated anti-clockwise relative to lower housing portion 3 (as viewed from above). Lug 14 bears against the leading end of rib 12 and causes reservoir 9 and metering member 10 to rotate with upper housing portion 2. As a result of this rotation, tongue 19 rides up helical ramp 18, causing reservoir 9 to move axially upwards, and lug 14 to move out of abutment with rib 11 and across the face of the leading edge of rib 12. The rotational movement further tensions spring 28 (for example so that it exerts a force of 10N).

Figure 8:
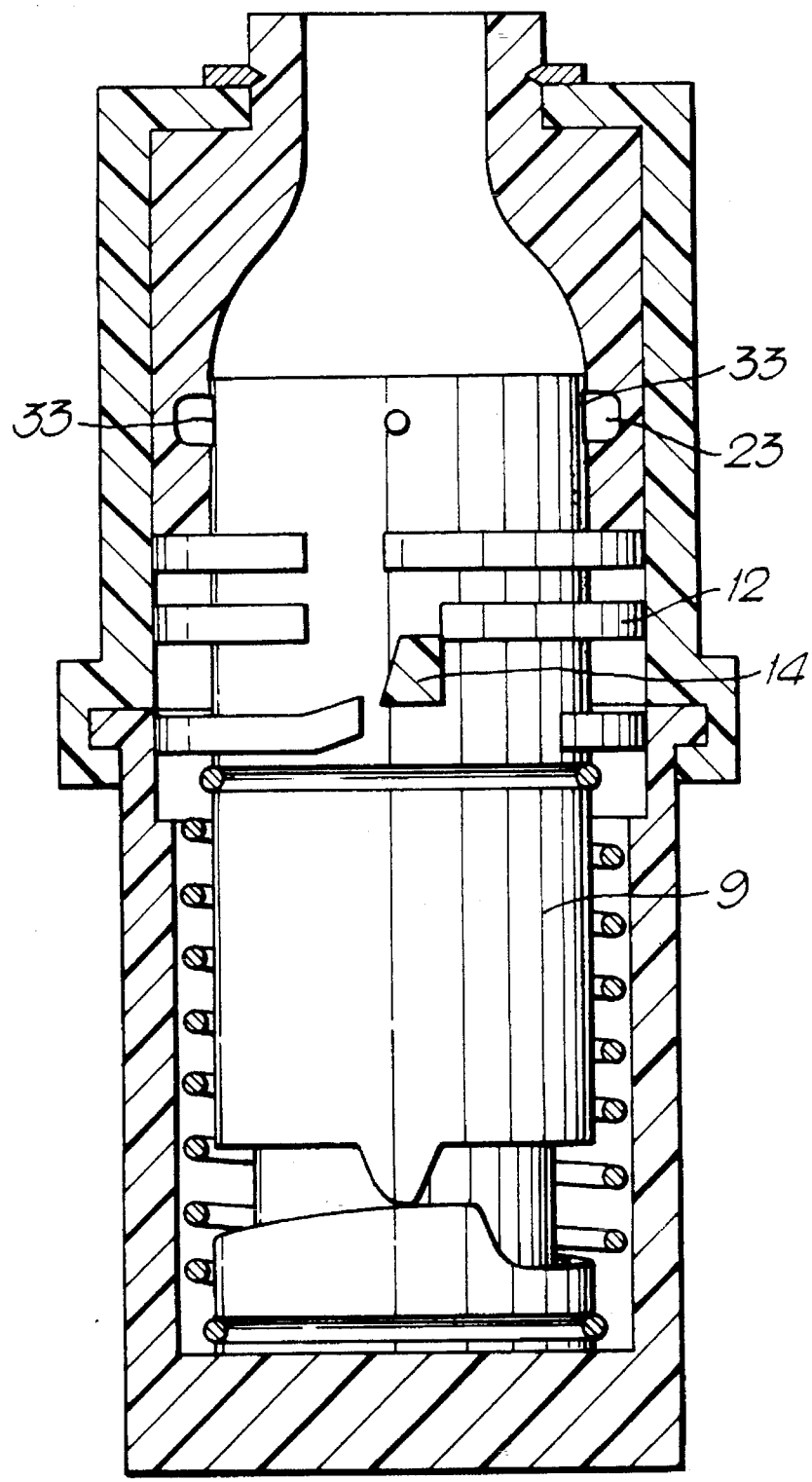
FIG. 8 is a view similar to that of FIG. 2 but showing the device in a metering position immediately prior to a charging rotation of the reservoir.

The upward movement of reservoir 9 continues as upper housing portion 2 is rotated until lug 14 no longer abuts the leading edge of rib 12. In this metering position, outlets 33 of reservoir 9 are in register with metering cups 23 of metering member 10. The position of reservoir 9 at the end of activation of the device and immediately prior to its charging rotation is shown in FIG. 8. Reservoir 9 is now free to rotate in a clockwise direction under the force of torsion spring 28 as it relaxes, and medicament is flung by centrifugal force through outlets 33 and into metering cups 23. During this charging rotation, lug 14 passes between ribs 12 and 13 as they rotate, and after rotating through almost 360° ramp 15 strikes lug 14 and deflects reservoir 9 back to the dosing position.

A patient then receives the metered medicament by inhaling at mouthpiece 6. This draws air in through air inlets 24 and 25 which then impinges on the medicament held in metering cups 23, causing the medicament to be entrained into the airstream and then inhaled.

If desired or necessary, an outer mouthpiece structure may be provided so that inhalation does not take place from mouthpiece 6 directly, thus preventing accidental rotation of mouthpiece 6 when inserted into the patient's mouth.

I claim:

1. A device for the administration by inhalation of a medicament in dry powder form, which comprises:

(a) a housing;

(b) a medicament reservoir, having an interior, mounted in the housing for rotation relative to said housing;

(c) means to rotate the reservoir relative to said housing about an axis within said housing; and (d) medicament metering means mounted in the housing for concerted rotation with the reservoir, said metering means including a metering chamber located radially of the axis and communicable with the reservoir;

in which the metering chamber is charged with medicament by the centrifugal force generated by rotation of the reservoir.

2. A device as claimed in claim 1, wherein the reservoir and the metering chamber are relatively displaceable between a metering position and a dosing position such that in the metering position the metering chamber communicates with the reservoir, and in the dosing position the metering chamber communicates with a mouthpiece.

3. A device as claimed in claim 1, further including means permitting said reservoir to be displaceable relative to the housing along the axis.

4. A device as claimed in claim 1, wherein the metering chamber is a cavity in the metering means.

5. A device as claimed in claim 1, wherein the interior of the reservoir comprises a main body and an outlet portion communicating with an outlet of the reservoir, the main body and the outlet portion communicating via a neck, the arrangement being such that the movement of medicament from the outlet portion to the main body of the reservoir is inhibited.

6. A reservoir for use in a device as claimed in claim 1, wherein the interior of the reservoir comprises:

(a) a main body; and (b) an outlet portion communicating with the main body via a neck, the arrangement being such that the movement of medicament from the outlet portion to the main body of the reservoir is inhibited.

7. A device as claimed in claim 1 wherein said means to rotate the medicament reservoir comprises a biasing means, which can be activated by rotation of the reservoir about the axis, relaxation of said biasing means after being activated serving to rotate the medicament reservoir.

8. A device for the administration by inhalation of a medicament in dry powder form, which comprises:

(a) a housing;

(b) a medicament reservoir, having an interior, mounted in the housing for rotation relative to said housing;

(c) means to rotate the reservoir relative to said housing about an axis within said housing;

(d) biasing means activated by rotation of the reservoir about the axis; and (e) medicament metering means including a metering chamber located radially of the axis and communicable with the reservoir;

in which the metering means is mounted in the housing for concerted rotation with the reservoir and the metering chamber is charged with medicament by the centrifugal force generated by rotation of the reservoir, wherein the reservoir and the metering chamber are relatively axially displaceable between a metering position and a dosing position such that in the metering position the metering chamber communicates with the reservoir, and in the dosing position the metering chamber communicates with a mouthpiece, wherein the means to rotate the medicament reservoir comprises relaxation of an activated biasing means which is activated by rotation of the reservoir about the axis, and wherein relative displacement of the metering chamber and the reservoir from the dosing position to the metering position occurs during activation of the biasing means.

* * * * *